United States Patent [19]

Curé

[11] 4,211,117

[45] Jul. 8, 1980

[54] MOLTEN METAL SAMPLING DEVICE

[75] Inventor: Omer P. I. Curé, Diepenbeek, Belgium

[73] Assignee: Electro-Nite Co., Philadelphia, Pa.

[21] Appl. No.: 970,583

[22] Filed: Dec. 18, 1978

[30] Foreign Application Priority Data

Mar. 30, 1978 [FR] France .................. 78 09327

[51] Int. Cl.² .............................................. G01N 1/12
[52] U.S. Cl. .......................... 73/425.4 R; 73/DIG. 9
[58] Field of Search .................. 73/425.4 R, DIG. 9

[56] References Cited

U.S. PATENT DOCUMENTS

| 3,452,602 | 7/1969 | Hackett | 73/DIG. 9 X |
|---|---|---|---|
| 3,913,404 | 10/1975 | Boron | 73/425.4 R |
| 3,967,505 | 7/1976 | Feichtinger | 73/DIG. 9 X |
| 4,002,074 | 1/1977 | Collins | 73/425.4 R |
| 4,084,441 | 4/1978 | McDevitt | 73/425.4 R |
| 4,120,204 | 10/1978 | Curé | 73/425.4 R |

Primary Examiner—Gerald Goldberg
Assistant Examiner—Joseph W. Roskos
Attorney, Agent, or Firm—Seidel, Gonda, Goldhammer & Panitch

[57] ABSTRACT

A molten metal sampling device having an inlet and an outlet is provided with a barrier partially obstructing the outlet for solidifying molten metal on contact therewith while permitting escape of gases.

6 Claims, 3 Drawing Figures

U.S. Patent     Jul. 8, 1980     4,211,117
FIG. 1
FIG. 2
FIG. 3
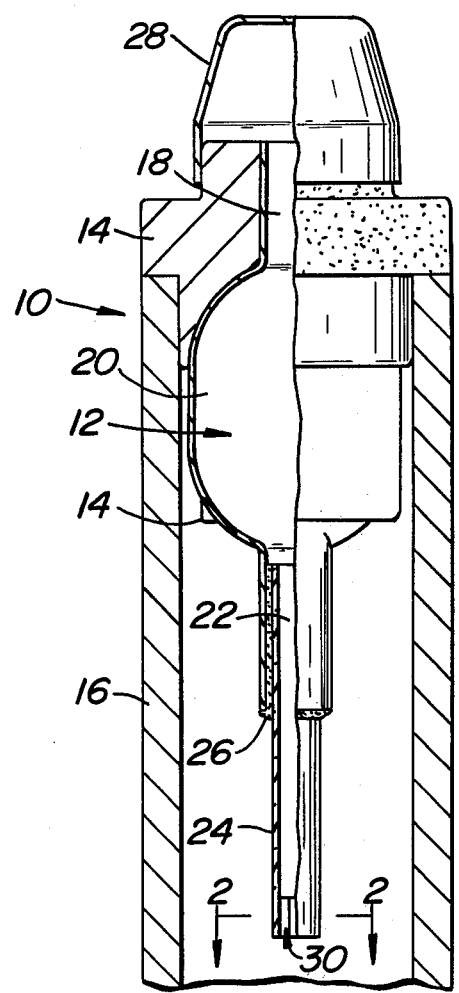
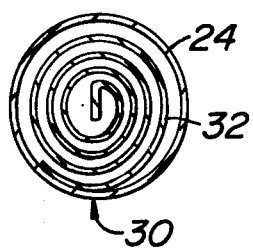
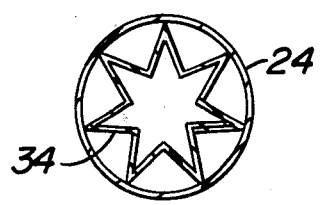

MOLTEN METAL SAMPLING DEVICE

BACKGROUND

The present invention is directed to a molten metal sampling device such as that disclosed in my U.S. Pat. No. 4,120,204. A typical sampling device includes a mold supported at one end of a tube for immersion into a bath of molten metal below any slag layer. As molten metal enters the mold, air from within the mold must escape. In order to produce a suitable sample, it is a requirement that the mold should be completely filled. Due to this requirement, it is difficult to avoid overflowing the mold by the metal passing out through the vent. Overflowing presents a problem in opening the mold and in time lost in preparing a sample.

One manner in which venting of air from the mold is shown in FIGS. 6 and 7 of said U.S. patent wherein a cylindrical extension of the chamber is necked down to an air discharge port. Control of air venting in that manner is difficult to attain since the vent must be of sufficient cross-section in order to readily permit discharge of air while preventing discharge of molten metal.

SUMMARY OF THE INVENTION

The molten metal sampling device of the present invention includes a mold having an inlet and an outlet. A barrier means partially obstructs the outlet for solidifying molten metal on contact therewith while permitting escape of gases. The barrier means has a plurality of air passages whose total area is at least 50% of the area of the outlet at the location of the barrier means.

In a preferred embodiment of the present invention, the barrier means is a strip of spring steel which has been coiled or corrugated and inserted into the outlet so that its own tension retains the barrier in place.

It is an object of the present invention to provide a molten metal sampling device with a novel barrier means which is simple, inexpensive and reliable.

Other objects will appear hereinafter.

For the purpose of illustrating the invention, there is shown in the drawings a form which is presently preferred; it being understood, however, that this invention is not limited to the precise arrangements and instrumentalities shown.

FIG. 1 is a partial vertical sectional view of a device in accordance with the present invention.

FIG. 2 is a sectional view taken along the line 2—2 in FIG. 1 but on an enlarged scale.

FIG. 3 is a sectional view similar to FIG. 2 but showing another embodiment.

Referring to the drawings in detail, wherein like numerals indicate like elements, there is shown in FIG. 1 a sampling device designated generally as 10. The device 10 includes a metal mold 12 made from two identical shelves which face each other and are separable along a parting line. The mold 12 is mounted within a support 14 made from a material such as foundry sand. The support 14 is inserted into the end of a paperboard tube 16 at one end thereof. The other end of tube 16 is adapted to be telescoped over a lance not shown so as to facilitate immersion of the mold end of tube 16 into a bath of molten metal and below any slag layer associated with the molten metal.

The mold 12 has an inlet defined by an intake passage 18 communicating at one end with the chamber 20. At its other end, the passage 18 is open and protected by a consummable metallic cap 28 attached to the support 14. The mold 12 has an outlet defined by passage 22. Passage 22 is defined by a tube 24 secured at one end within a cylindrical extension of the mold 12 by way of cement 26 or the like. Tube 24 is preferably made from a vitreous material such as quartz.

The device 10 as thusly described is in all essential respects disclosed in U.S. Pat. No. 4,120,204. The tube 24 is provided with a uniform internal transverse dimension and contains a barrier means designated generally as 30. The barrier means 30 partially obstructs that portion of the outlet of mold 12 defined by tube 24 for solidifying molten metal on contact therewith while permitting escape of gases. A preferred form or embodiment of the barrier means 30 is a spirally wound strip of spring steel 32. See FIG. 2. Preferably, the entirety of the strip of spring steel 32 is disposed within the tube 24. The strip of spring steel 32 is related to the cross-sectional area of tube 24 in a manner so that at least 50% and preferably 70% of the area of tube 24 is unobstructed for free flow of gases.

The width of the strip of spring steel 32 is such that the total area of the strip is approximately 5 to 10 times the cross-sectional area of tube 24. In this manner, gases such as air can freely escape from the mold 12 when the latter is being filled during immersion in the molten metal. As soon as the molten metal reaches strip 32, it solidifies on contact therewith thereby preventing any overflowing of the mold 12 and assuring a full sample. The strip 32 does not require any means for fixedly securing the same within the tube 24. The uncoiling force of strip 32 which preferably is about 1.5 Kg. is sufficient to maintain the strip 32 in position within tube 24 without any external securement means. It will be noted that strip 32 as shown more clearly in FIG. 2 resembles the main spring of a watch or clock.

As shown more clearly in FIG. 3, the barrier means 30 may be a corrugated metal strip of spring steel 34 which, except for its corrugations, has the other attributes of strip 32 described above. The tendency of strip 34 to uncoil provides sufficient force to maintain the strip 34 in the desired location within the tube 24. Thus, each of the strips 32 and 34 are wound before being positioned within tube 24. Other configurations of a barrier means will be apparent to those skilled in the art.

There are a number of parameters which influence the results attainable by a molten metal sampling device including the type of metal, the temperature of the metal, the immersion speed and depth, the viscosity of the molten metal, and the diameter of the tube 24. The barrier means should have sufficient mass and surface area to ensure causing solidification of the molten metal on contact therewith within about 5 seconds. Suitable dimensions for strip 32 are spring steel DIN 17222 having a thickness of about 0.2 mm, a width of about 5 mm, and a total uncoiled length of about 40 mm, with the strip coiled to a configuration shown in FIG. 2 with the inner diameter of tube 24 being approximately 6 mm and the radial distance between adjacent coils being between 0.5 mm and 1.5 mm.

The present invention may be embodied in other specific forms without departing from the spirit or essential attributes thereof and, accordingly, reference should be made to the appended claims, rather than to the foregoing specification, as indicating the scope of the invention.

I claim:

1. A molten metal sampling device comprising a mold having an inlet and an outlet, a barrier means partially obstructing said outlet for solidifying molten metal on contact therewith while permitting escape of gases, said barrier means having a plurality of air passages whose total area is at least 50% of the area of the outlet at the location of the barrier means, said barrier means being a pretensioned wound metallic strip exerting pressure radially outwardly against the inner surface of said outlet.

2. A device in accordance with claim 1 wherein said strip is spirally wound spring steel.

3. A device in accordance with claim 1 wherein said strip is a corrugated strip of spring steel.

4. A device in accordance with claim 1 wherein said air passages occupy about 70% of the space at the area of the outlet.

5. A device in accordance with claim 4 wherein said passages are parallel to one another and having transverse dimensions between 0.5 mm and 1.5 mm.

6. A molten metal sampling device comprising a mold having an inlet and an outlet, a barrier means partially obstructing said outlet for solidifying molten metal on contact therewith while permitting escape of gases, said barrier means being a wound metallic strip at least a portion of which exerts radially outwardly directed pressure against the inner surface of said outlet.

* * * * *